United States Patent
Iwamoto

(10) Patent No.: US 9,377,429 B2
(45) Date of Patent: Jun. 28, 2016

(54) CALIBRATION LIQUID

(71) Applicant: HORIBA, Ltd., Kyoto-shi, Kyoto (JP)

(72) Inventor: Yasukazu Iwamoto, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 386 days.

(21) Appl. No.: 13/727,378

(22) Filed: Dec. 26, 2012

(65) Prior Publication Data

US 2013/0168265 A1      Jul. 4, 2013

(30) Foreign Application Priority Data

Dec. 28, 2011      (JP) .................................. 2011-287803

(51) Int. Cl.
| | |
|---|---|
| G01N 27/28 | (2006.01) |
| G01N 27/416 | (2006.01) |
| G01N 33/493 | (2006.01) |
| G01N 27/333 | (2006.01) |

(52) U.S. Cl.
CPC ............ G01N 27/28 (2013.01); G01N 27/4163 (2013.01); G01N 33/493 (2013.01); G01N 27/333 (2013.01)

(58) Field of Classification Search
CPC .............................. G01N 27/28; G01N 27/333
See application file for complete search history.

(56) References Cited

U.S. PATENT DOCUMENTS

| | | | |
|---|---|---|---|
| 3,635,212 A | 1/1972 | Watanabe et al. | |
| 3,915,642 A | 10/1975 | Small et al. | |
| 4,626,512 A * | 12/1986 | Oku et al. | ......................... 436/8 |
| 4,713,165 A | 12/1987 | Conover et al. | |
| 4,806,486 A * | 2/1989 | Sprokholt | .......... G01N 27/4165 436/17 |
| 5,023,186 A * | 6/1991 | Herring | ........................... 436/11 |
| 5,227,305 A * | 7/1993 | Manzoni et al. | ................ 436/19 |
| 6,110,338 A * | 8/2000 | Rokugawa | ...................... 204/418 |
| 2010/0176006 A1* | 7/2010 | Bickford | .............. G01N 27/333 205/792.5 |

FOREIGN PATENT DOCUMENTS

| | | |
|---|---|---|
| CN | 1101978 A | 4/1995 |
| CN | 1504747 A | 6/2004 |
| EP | 0450473 A2 | 10/1991 |
| JP | 61-025049 * | 2/1986 |
| JP | 61025049 A | 2/1986 |
| JP | 03127252 U | 12/1991 |
| JP | 08500679 A | 1/1996 |

(Continued)

OTHER PUBLICATIONS

Wan et al. (Analytica Chimica Acta 525 (2004) 11-16).*
Khalil et al. (Analytical Letters 1986).*

(Continued)

*Primary Examiner* — Jennifer Dieterle
(74) *Attorney, Agent, or Firm* — Alleman Hall McCoy Russell & Tuttle LLP

(57) ABSTRACT

This invention relates to a correction liquid for a liquid membrane type ion-selective electrode that makes it possible to measure a ratio between a sodium ion concentration and a potassium ion concentration in urine by correcting for an influence from an ionic strength of the urine. The correction liquid comprises a sodium ion-sensitive part that selectively reacts with the sodium ion and a potassium ion-sensitive part that selectively reacts with the potassium ion, and measures a ratio between a sodium ion concentration and a potassium ion concentration in urine, and comprises the sodium ion, the potassium ion, and an electrolytic ionic strength modifier.

6 Claims, 3 Drawing Sheets

(56) References Cited

FOREIGN PATENT DOCUMENTS

JP          2004350861          12/2004
WO            9406019 A1         3/1994

OTHER PUBLICATIONS

Pelleg et al. (Clin. Chem. 1975).*
Machine translation jp61-025049, done Mar. 4, 2016.*
Diamond, D. et al., "Robust Estimation of Selectivity Coefficients Using Multivariate Calibration of Ion-Selective Electrode Arrays", Analytica Chimica Acta, vol. 276, Issue I, pp. 75-86, 12 pages.
Forster, R. et al., "Nonlinear Calibration of Ion-Selective Electrode Arrays for Flow Injection Analysis." Analytical Chemistry, vol. 64, Issue 15, pp. 1721-1728. Aug. 1992, 8 pages.
Vrouwe, E. et al., "Rapid Inorganic Ion Analysis Using Quantitative Microchip Capillary Exlectrophoresis." Journal of Chromatography A, vol. 1102, Issues 1-2, pp. 287-293, Jan. 2006, 8 pages.
European Patent Office, Extended European Search Report of EP12198185-6, Mar. 27, 2013, Germany, 7 pages.
Japanese Patent Office, Office Action Issued in Japanese Patent Application No. 2011-287803, Feb. 24, 2015, 2 pages.
State Intellectual Property Office of the People's Republic of China, First Office Action Issued in Chinese Patent Application No. 201210560822.6, Jan. 5, 2016, 9 pages.

* cited by examiner

CALIBRATION LIQUID

FIELD OF THE ART

This invention relates to a correction liquid for an ion-selective electrode that measures a ratio between a sodium ion concentration and a potassium ion concentration in urine.

BACKGROUND ART

Sodium ions and potassium ions are contained in urine, and it is said that a ratio between the sodium ion concentration and the potassium ion concentration is strongly correlated with blood pressure. Accordingly, it is thought that the blood pressure can be easily controlled by measuring the ratio between the sodium ion concentration and the potassium ion concentration in urine (patent document 1).

A method for measuring an ion concentration in a sample solution includes an ion electrode method that measures a change in an electric potential of an electrode in accordance with a change in an ion analyte concentration (to be exact, activity of the ion to be analyzed) in the sample solution through a sensitive part that selectively reacts with the ion analyte and obtains the concentration of the ion analyte in the sample solution.

PRIOR ART DOCUMENT

Patent document 1 Japanese Unexamined Patent Application Publication No. 2004-350861

DISCLOSURE OF THE INVENTION

Problems to be Solved by the Invention

However, since the measurement by the ion electrode method is influenced by the ionic strength of the sample solution, there might be a case where an accurate measurement value is not obtained. For example, since an amount of the sodium ions contained in urine is small, about 1/20 to 1 of the potassium ions, the measurement value in the case where the analyte is sodium ion is likely affected by the ionic strength. As a result, in order to measure the ratio between the sodium ion concentration and the potassium ion concentration with high accuracy, it becomes necessary to correct the influence from the ionic strength in the sample solution.

Accordingly, the present claimed invention intends to provide a correction liquid for an ion-selective electrode that makes it possible to measure the ratio between the sodium ion concentration and the potassium concentration in urine with high accuracy by correcting for the influence from the ionic strength in urine.

Means to Solve the Problems

A correction liquid in accordance with this invention is a correction liquid for an ion-selective electrode that measures a ratio between a sodium ion concentration and a potassium ion concentration in urine comprising a sodium ion-sensitive part that selectively reacts with a sodium ion and a potassium ion-sensitive part that selectively reacts with a potassium ion, and comprises the sodium ion, the potassium ion and an electrolytic ionic strength modifier electrolyte.

In accordance with this arrangement, it is possible to correct the ion-selective electrode by correcting an influence from the ionic strength of the urine by mixing the ionic strength modifier into the correction liquid so as to make the ionic strength of the correction liquid generally the same as that of the ionic strength of urine. As a result of this, it is possible to detect a small amount of the potassium ion accurately so that the ratio between the sodium ion concentration and the potassium ion concentration can be obtained with high accuracy by analyzing the sodium ion and the potassium ion in the urine by the use of the ion-selective electrode that is corrected by the correction liquid of this invention.

It is preferable that the sodium ion-sensitive part is a liquid membrane type ion-sensitive membrane wherein a sodium ionophore (a sodium ion-selective ligand) is supported by a base material and the potassium ion-sensitive part is a liquid membrane type ion-sensitive membrane wherein a potassium ionophore (a potassium ion-selective ligand) is supported by a base material, and the ionic strength modifier contains a bivalent cation. Since the selectivity coefficient of the sodium ionophore and the selectivity coefficient of the potassium ionophore to the bivalent cation are low and the bivalent cation rarely reacts with the sodium ionophore and the potassium ionophore, even though the bivalent cation is contained in the correction liquid, there is no influence on the correction.

A representative example of the bivalent cation is an alkaline earth metal ion such as, for example, a magnesium ion and a calcium ion.

In case of correction or measurement, the ion-selective electrode is used together with a reference electrode, and it is preferable that the ionic strength modifier contains an ion that is the same as that of an internal solution for the ion-selective electrode and that of an internal solution for the reference electrode. Since the ionic strength modifier contains the same ion as that of the internal solution for the ion-selective electrode and that of the internal solution for the reference electrode, it is possible both to minimize the fluctuation of the electric potential difference between the correction liquid and the internal solution for the reference electrode and to counterbalance an influence on the electric potential of the ion-selective electrode from the internal solution for the ion-selective electrode with an influence from the internal solution for the reference electrode. For example, an anion such as a chloride ion, a nitrate ion and a sulphate ion are representative examples of the above-mentioned ion. Among them, in the case where the inner electrode for the reference electrode comprises a metal body and a slightly soluble salt membrane made of a slightly soluble salt of the metal constituting the metal body, the anion constituting the slightly soluble salt is preferable.

Representative examples of the ionic strength modifier are, for example, a chloride containing a bivalent cation, a nitrate containing a bivalent cation and a sulphate containing a bivalent cation. A suitable ionic strength modifier depends on the type of the inner electrode, and, for example, (1) in the case of using an Ag/AgCl electrode or an $Hg/Hg_2Cl_2$ electrode as the inner electrode, it is preferable to use the chloride containing the bivalent cation, (2) in the case of using a liquid membrane type electrode wherein a predetermined ionophore is supported by a base material as the inner electrode, it is preferable to use the chloride containing the bivalent cation, the nitrate containing the bivalent cation or the sulphate containing the bivalent cation as the inner electrode, and (3) in case of using an $Hg/Hg_2SO_4$ electrode as the inner electrode, it is preferable to use the sulphate containing the bivalent cation.

Representative examples of the chloride containing the bivalent cation are, for example, magnesium chloride and calcium chloride. Representative examples of the nitrate containing the bivalent cation are, for example, magnesium nitrate and calcium nitrate. Representative examples of the sulphate containing the bivalent cation represented are, for example, magnesium sulphate and calcium sulphate. Among them, a highly water soluble salt is preferable.

In this invention, it is preferable that the internal solution of the ion-selective electrode and the internal solution of the reference electrode contain the ionic strength modifier to adjust ionic activity of the internal solution. If the ionic activity of the internal solution of the ion-selective electrode, the ionic activity of the internal solution of the reference electrode and the ionic activity of the correction liquid are all generally the same, since it is possible to formulate the correction liquid corresponding to an isothermal intersection point (zero point), it is possible for the electrode to be unaffected by a temperature change.

Effect of the Invention

In accordance with this invention having the above arrangement, it is possible to measure the ratio between the sodium ion concentration and the potassium ion concentration in urine with high accuracy by correcting for the influence of the ionic strength in urine.

BEST MODES OF EMBODYING THE INVENTION

One embodiment of this invention will be explained with reference to the drawings.

Figure 1:
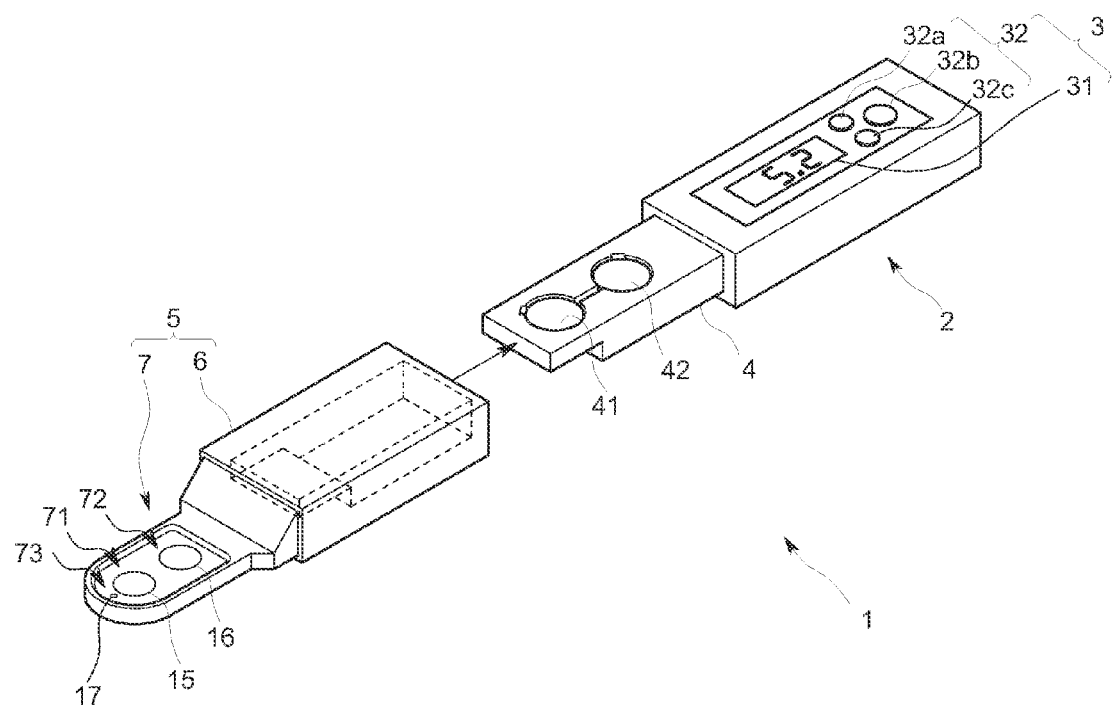
FIG. 1 is an exploded perspective view showing a structure of a liquid membrane type $Na^+/K^+$ electrode in accordance with one embodiment of this invention.
Figure 2:
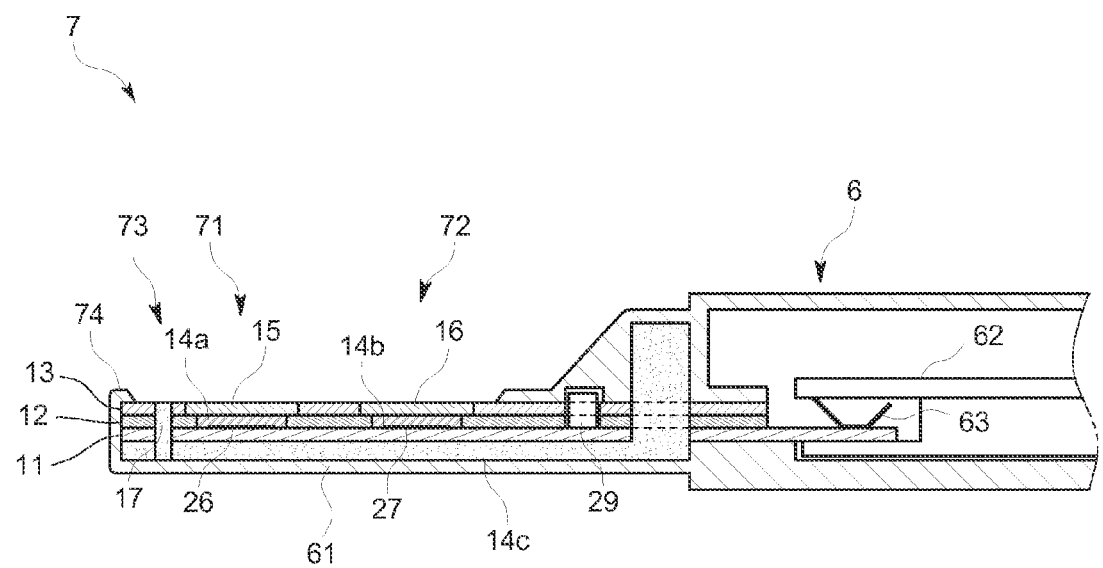
FIG. 2 is a longitudinal cross-sectional view showing a structure of a flat-type sensor of this embodiment.
Figure 3:
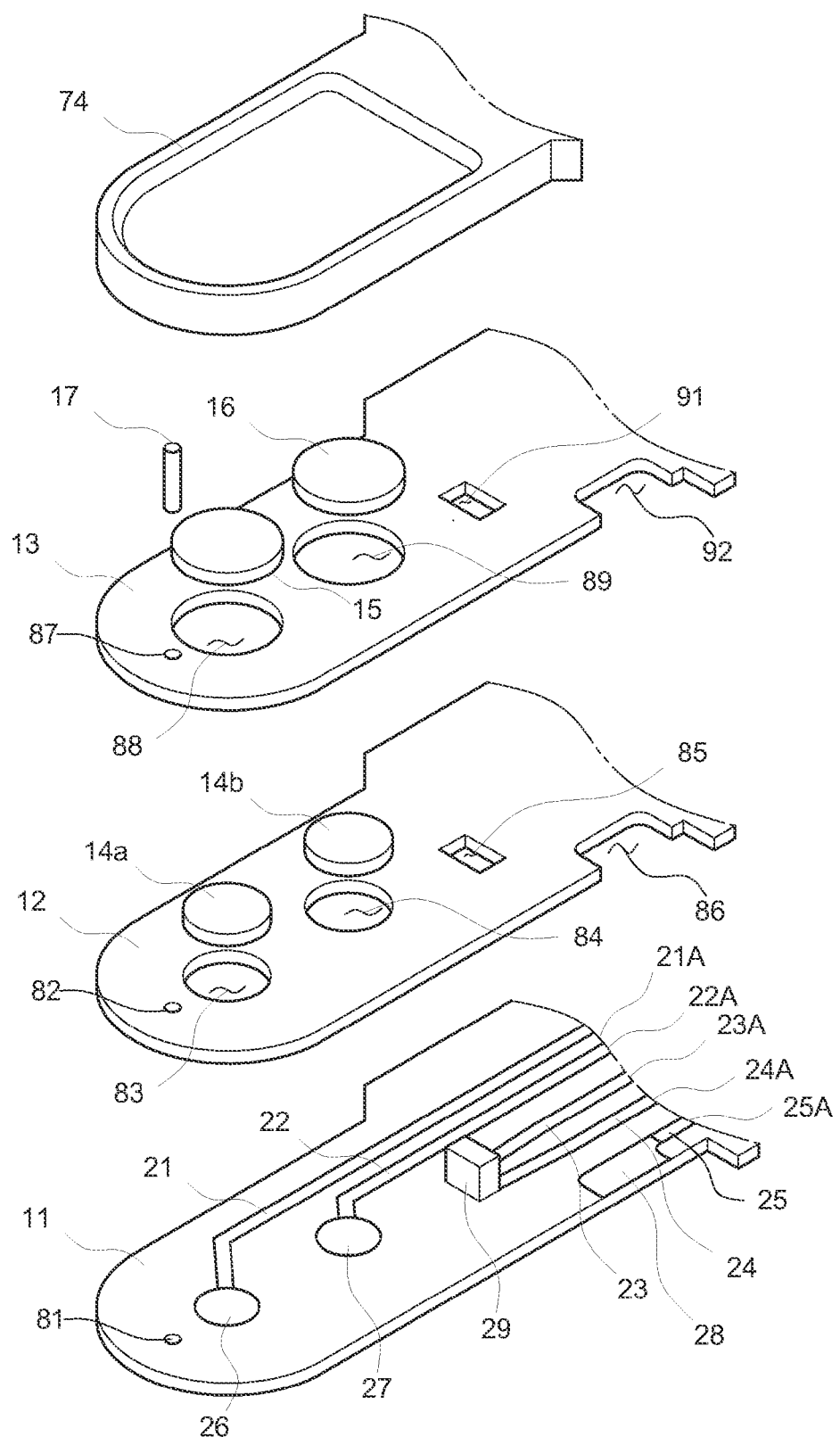
FIG. 3 is an exploded perspective view showing a principal part of the flat-type sensor of this embodiment.

A liquid membrane type $Na^+/K^+$ electrode 1 in accordance with this embodiment is a hybrid type wherein an ion-selective electrode and a reference electrode are integrated for measuring a ratio of a concentration of a sodium ion and a concentration of a potassium ion in, for example, urine, and as shown in FIG. 1~3, comprises a body 2 made of a resin, an arithmetic processing part (not shown in drawings) such as a micro computer incorporated in the body 2, a display/operation part 3 formed on an upper surface of the body 2, a power source part 4 formed adjacent to the display/operation part 3 and an electrode part 5 made of a synthetic resin and formed in a water-proof structure.

Lead parts 21A, 22A, 23A 24A, and 25A of a flat-type sensor 7, to be described later, and a connecting part 63 that is connected to a circuit substrate 62 having the arithmetic processing part are provided inside of the body 2. The circuit substrate 62 is connected to and supported by a case.

The display/operation part 3 comprises a display part 31 and an operation part 32 that operates various buttons such as a power button 32a, a correction button 32b and a hold button 32c. The power source part 4 comprises button batteries 41, 42.

The electrode part 5 comprises a tubular part 6 whose one end opens to make it possible to house the power source part 4 and a flat-type sensor 7 that is continuously arranged at the other end of the tubular part 6. The electrode part 5 is configured so that it can be integrally connected with the body 2 by being mounted on the body 2 so as to cover the power source part 4 or so that it can be separated from the body 2.

The flat-type sensor 7 is, as shown in FIG. 2 and FIG. 3, made of a material such as polyethylene terephthalate having electrical insulation, and comprises substrates 11, 12, and 13 each of which is laminated. A part of each substrate 11, 12, and 13 is formed in a shape of an arc. The third substrate 13 positioned as the top layer and the second substrate 12 positioned as the middle layer have the same shape (in plane view), and the arc part of the first substrate 11 positioned as the lower layer is the same as that of the second substrate 12 and the third substrate 13, and other side of the first substrate 11 is longer than that of the second substrate 12 and the third substrate 13. In addition, a detected liquid holder 74 is arranged to surround a peripheral border of the third substrate 13.

Conductive parts 21, 22, 23, 24, and 25 are formed on an upper surface of the first substrate 11 by silk-screen printing, for example, Ag paste after providing a predetermined pretreatment, and a circular through bore 81 is formed on the first substrate 11. The conductive parts 21, 22, 23, 24, and 25 are processed as follows. First, a distal end of the conductive part 21 located at one of the outer sides is covered with AgCl and a circular inner electrode 26 of a $Na^+$ electrode 71 is formed, and a distal end of the conductive part 22 located at an inner side of the conductive part 21 is also covered with AgCl and a circular inner electrode 27 of a $K^+$ electrode 72 is formed. In addition, a distal end of the conductive part 25 located at the other outer side is also covered with AgCl and an inner electrode 28 of a reference electrode 73 having an elongated shape located at one of the side end parts of the substrate 11 is formed. Furthermore, a temperature compensating element 29 such as a thermistor is arranged over a distal end of the conductive part 23 and a distal end of the conductive part 24, wherein the conductive parts 23 and 24 are located at an inner side. The other ends of each conductive part 21, 22, 23, 24, and 25 constitute leads part 21A, 22A, 23A, 24A, and 25A.

The second substrate 12 is provided with a through bore 82 that is arranged at a position corresponding to the through bore 81 and that has the same diameter as that of the through bore 81 and through bores 83 and 84, each of which is formed at a position corresponding to each of the inner electrode 26 and inner electrode 27 and whose diameters are a little larger than those of the through bores 81 and 82, and a rectangular through bore 85 that is formed at a position corresponding to the temperature compensating element 29 and whose size is generally the same as that of the temperature compensating element 29. Furthermore, an elongated cutout 86 is formed at a side end part corresponding to the inner electrode 28 of the reference electrode 73.

The third substrate 13 is provided with a through bore 87 that is arranged at a position corresponding to the through bores 81 and 82 and that has the same diameter as that of the through bores 81 and 82, through bores 88 and 89 each of which is formed at a position corresponding to each of the through bore 83 and the through bore 84 and whose diameter is a little larger than that of the through bores 83 and 84, and a rectangular through bore 91 that is formed at a position corresponding to the through bore 85 and whose size is generally the same as that of the through bore 85. Furthermore, a cutout 92 whose size is the same as that of the cutout 86 is formed at a position corresponding to the cutout 86.

A liquid junction 17 of the reference electrode 73 composed of a porous body made of polyethylene is inserted into the through bores 81, 82, and 87, each of which is formed at the corresponding position of each of the substrates 11, 12, and 13 respectively. The liquid junction 17 is mounted in a state that the upper surface of the liquid junction 17 is generally flush with an upper surface of the third substrate 13 positioned as the top layer.

A gelled internal solution 14a is mounted on the through bore 83 formed on the second substrate 12 and a gelled internal solution 14b is mounted on the through bore 84 on the second substrate 12. The gelled internal solution 14a is formed into a disk shape and made of a pH buffer solution containing $CaCl_2$ to which a sodium ion is added and to which agar as a gelatinizing agent and glycerin as a gel evaporation retardant are further added. The gelled internal solution 14b is formed into a disk shape and made of a pH buffer solution containing $CaCl_2$ to which a potassium ion is added and to which agar as a gelatinizing agent and glycerin as a gel evaporation retardant are further added. A chloride ion concentration of the internal solution is adjusted to 1M. The gelled internal solution 14a is mounted inside of the through bore 83 in a state that an upper surface of the gelled internal solution 14a projects a little from an upper surface of the second substrate 12, and makes contact with the inner electrode 26 formed on an upper surface of the first substrate 11 through the through bore 83. The gelled internal solution 14b is mounted inside of the through bore 84 in a state that an upper surface of the gelled internal solution 14b projects a little from an upper surface of the second substrate 12, and makes contact with the inner electrode 27 formed on the upper surface of the first substrate 11 through the through bore 84.

A disk shaped sodium ion-sensitive membrane 15 is mounted on the through bore 88 formed on the third substrate 13 and the sodium ion-sensitive membrane 15 makes contact with the gelled internal solution 14a and is fixed to the third substrate 13 in a state that an upper surface of the gelled internal solution 14a is generally flush with the upper surface of the third substrate 13. A disk shaped potassium ion-sensitive membrane 16 is mounted on the through bore 89 formed on the third substrate 13 and the potassium ion-sensitive membrane 16 makes contact with the gelled internal solution 14b and is fixed to the third substrate 13 in a state that the upper surface of the gelled internal solution 14b generally flush with the upper surface of the third substrate 13.

The solid sodium ion-sensitive membrane 15 is formed with a procedure of adding a plasticizer and Bis (12-crown-4) as a sodium ionophore to polyvinyl chloride (PVC), dissolving the polyvinyl chloride to which the plasticizer and Bis (12-crown-4) are added with an organic solvent such as tetrahydrofuran (THF), filling the dissolved polyvinyl chloride into the through bore 88 by means of potting or an ink jet printing method, and heating so as to evaporate the organic solvent.

The potassium ion-sensitive membrane 16 is formed by the same method as that of the sodium ion-sensitive membrane 15 except for using Bis (benzo-15-crown-5) as a potassium ionophore.

A gelled internal solution 14c of the reference electrode 73 is arranged from below the first substrate 11 locating at the lowest layer to the upside of the third substrate 13 locating at the top layer in a case 61 continuously arranged to the tubular part 6. The gelled internal solution 14c is so filled that an upper part and a lower part of the gelled internal solution 14c are in communication through a gap between a side part, in the internal electrode 28 side of the reference electrode 73, of the substrates 11, 12, and 13 and the case 61, and the gelled internal solution 14c makes contact with a surface of the inner electrode 28 of the reference electrode 73 and the lower end part of the liquid junction 17. The gelled internal solution 14c of the reference electrode 73 is an internal solution comprising an $NH_4Cl$ aqueous solution of concentration 1M to which agar as the gelling agent and glycerin as the gel evaporation retardant are added.

In order to measure a ratio between the sodium ion concentration and the potassium ion concentration in urine using the liquid membrane type Na+/K+ electrode 1, an adequate amount of urine is first dripped on the sodium ion-sensitive membrane 15 and the potassium ion-sensitive membrane 16. Subsequently, an electromotive force is generated at the sodium ion-sensitive membrane 15 in accordance with a difference between an ionic concentration of the gelled internal solution 14a and an ionic concentration of the urine and an electromotive force is generated at the potassium ion-sensitive membrane 16 in accordance with a difference between an ionic concentration of the gelled internal solution 14b and the ionic concentration of the urine. Each of the electromotive forces is detected as an electric potential difference between the internal electrode 26 of the Na+ electrode 71 and the internal electrode 28 of the reference electrode 73, and an electric potential difference between the internal electrode 27 of the K+ electrode 72 and the internal electrode 28 of the reference electrode 73 respectively. Next, the ratio between the sodium ion concentration and the potassium ion concentration is calculated by the arithmetic processing part based on the electromotive force, and the ratio is displayed on the display part 31.

The correction liquid to correct the liquid membrane type $Na^+/K^+$ electrode 1 contains calcium chloride as the ionic strength modifier in addition to sodium ion and potassium ion. A quantity of the ionic strength modifier mixture is adjusted so as to make the chloride ion concentration of this correction liquid 0.2 M. The reason why the chloride ion concentration of the correction liquid of this invention is 0.2M while the chloride ion concentration of the gelled internal solution 14c of the reference electrode 73 is 1M is that glycerin is added to the gelled internal solution 14c of the reference electrode 73 and glycerin reduces the activity of the chloride ion.

In accordance with the correction liquid having the above arrangement, since the ionic strength modifier is mixed so as to make the corrected ionic strength generally the same as the ionic strength of urine, it is possible to correct the liquid membrane type $Na^+/K^+$ electrode 1 for the influence of the ionic strength of the urine. As a result of this, it is possible to detect a small amount of the potassium ion accurately so that the ratio between the sodium ion concentration and the potassium ion concentration can be obtained with high accuracy by analyzing the sodium ion and the potassium ion in the urine using the liquid membrane type $Na^+/K^+$ electrode 1 that is corrected by the correction liquid of this invention.

The present claimed invention is not limited to the above-mentioned embodiment, and a part or all of the above-mentioned embodiment or the modified embodiment can be combined without departing from a spirit of this invention.

EXPLANATION OF REFERENCE CHARACTERS

1 . . . liquid membrane type $Na^+/K^+$ electrode
15 . . . sodium ion-sensitive membrane
16 . . . potassium ion-sensitive membrane
71 . . . $Na^+$ electrode
72 . . . $K^+$ electrode

The invention claimed is:
1. A calibration system, comprising:
an ion-selective electrode, electrically coupled to a reference electrode and operatively coupled to a processor and a display, comprising a sodium ion-sensitive part that selectively reacts with sodium ions, and a potassium ion-sensitive part that selectively reacts with potassium ions, wherein the sodium ion-sensitive part is a liquid membrane type ion-sensitive membrane wherein a sodium ionophore is supported by a base material and the potassium ion-sensitive part is a liquid membrane type ion-sensitive membrane wherein a potassium ionophore is supported by a base material;

a urine sample applied to the liquid membranes of the ion-selective electrode, a calibration liquid, including sodium and potassium ions, applied to the liquid membranes of the ion-selective electrode before the urine sample is applied to the liquid membranes of the ion-selective electrode, and an electrolytic ionic strength modifier mixed into the calibration liquid before the urine sample is applied to the liquid membranes of the ion-selective electrode, until the calibration liquid has an ionic strength that is substantially equal to an ionic strength of another urine sample;

wherein the processor, operatively coupled to the ion-selective electrode and the display, is configured to detect electrical signals from the ion-selective electrode and calculate a ratio between a sodium ion concentration and a potassium ion concentration in the urine sample based on the electrical signals, wherein the display, operatively coupled to the processor, is configured to display the ratio between the sodium ion concentration and the potassium ion concentration in the urine sample;

wherein the electrolytic ionic strength modifier contains ions that are identical to ions of an internal solution for the ion-selective electrode and ions of an internal solution for the reference electrode, and wherein the ions of the electrolytic ionic strength modifier are identical to ions contained in the other urine sample.

2. The calibration system described in claim 1, wherein the ionic strength modifier contains a bivalent cation.

3. The calibration system described in claim 1, wherein the internal solution of the ion-selective electrode and the internal solution of the reference electrode contain the ionic strength modifier to adjust an ionic activity of the internal solution.

4. The calibration system described in claim 1, wherein the ionic strength modifier is a chloride containing a bivalent cation, a nitrate containing a bivalent cation or a sulphate containing a bivalent cation.

5. The calibration system described in claim 4, wherein the calibration liquid is applied to liquid membranes of the reference electrode before the urine sample is applied to the liquid membranes of the reference electrode, and the electrolytic ionic strength modifier is mixed into the calibration liquid that is applied to liquid membranes of the reference electrode.

6. A method for calibrating an ion-selective electrode, electrically coupled to a reference electrode and operatively coupled to a processor and a display, the ion-selective electrode comprising a sodium ion-sensitive part that selectively reacts with sodium ions, and a potassium ion-sensitive part that selectively reacts with potassium ions, wherein the sodium ion-sensitive part is a liquid membrane type ion-sensitive membrane wherein a sodium ionophore is supported by a base material and the potassium ion-sensitive part is a liquid membrane type ion-sensitive membrane wherein a potassium ionophore is supported by a base material, the method comprising:

applying a urine sample to the liquid membranes of the ion-selective electrode, applying a calibration liquid, including sodium and potassium ions, to the liquid membranes of the ion-selective electrode before the urine sample is applied to the liquid membranes of the ion-selective electrode, and mixing an electrolytic ionic strength modifier mixed into the calibration liquid before the urine sample is applied to the liquid membranes of the ion-selective electrode, until the calibration liquid has an ionic strength that is substantially equal to an ionic strength of another urine sample;

wherein the processor, operatively coupled to the ion-selective electrode and the display, is configured to detect electrical signals from the ion-selective electrode and calculate a ratio between a sodium ion concentration and a potassium ion concentration in the urine sample based on the electrical signals, wherein the display, operatively coupled to the processor, is configured to display the ratio between the sodium ion concentration and the potassium ion concentration in the urine sample;

wherein the electrolytic ionic strength modifier contains ions that are identical to ions of an internal solution for the ion-selective electrode and ions of an internal solution for the reference electrode, and wherein the ions of the electrolytic ionic strength modifier are identical to ions contained in the other urine sample.

* * * * *